(12) United States Patent
Saville

(10) Patent No.: US 6,740,073 B1
(45) Date of Patent: May 25, 2004

(54) GUIDING CATHETER REINFORCEMENT WITH ANGLED DISTAL END

(75) Inventor: Steven T. Saville, Murrieta, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 113 days.

(21) Appl. No.: 09/731,525

(22) Filed: Dec. 6, 2000

(51) Int. Cl.⁷ .............................................. A61M 25/00
(52) U.S. Cl. ..................................................... 604/524
(58) Field of Search ............................... 606/200, 192; 604/527

(56) References Cited

U.S. PATENT DOCUMENTS

| | | | |
|---|---|---|---|
| 5,662,621 A | | 9/1997 | Lafontaine .................. 604/281 |
| 5,906,606 A | * | 5/1999 | Chee et al. .................. 604/527 |
| 5,951,929 A | | 9/1999 | Wilson ........................ 264/139 |
| 5,972,019 A | * | 10/1999 | Engelson et al. ........... 606/200 |
| 6,143,013 A | * | 11/2000 | Samson et al. ............. 604/264 |

* cited by examiner

*Primary Examiner*—Henry Bennett
*Assistant Examiner*—Sabrina Dagostino
(74) *Attorney, Agent, or Firm*—Fulwider Patton Lee & Utecht, LLP

(57) ABSTRACT

The invention is directed to a guiding catheter for intraluminal procedures, such as stent delivery, balloon dilatation, atherectomy and the like, and for advancing and delivering intraluminal devices within body lumens. The guiding catheter in accordance with the invention has a multi-strand braided reinforcement layer within the wall of the catheter that has a distal end which is at an angle of at least 15° from a transverse plane perpendicular to the longitudinal axis of the catheter. This construction of the reinforced braided layer assists in the retraction of an intraluminal device back into the inner lumen of the guiding catheter. The guiding catheter may have an inner layer that has a distal end that is also at an angle with respect to a transverse plane perpendicular to the longitudinal axis.

20 Claims, 2 Drawing Sheets

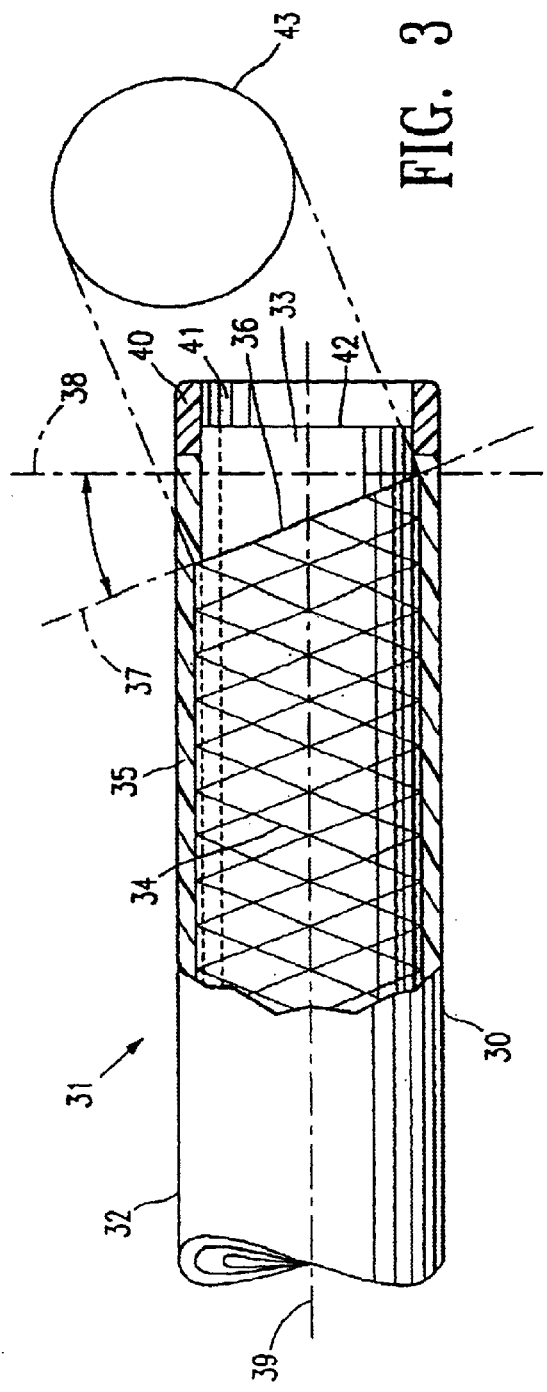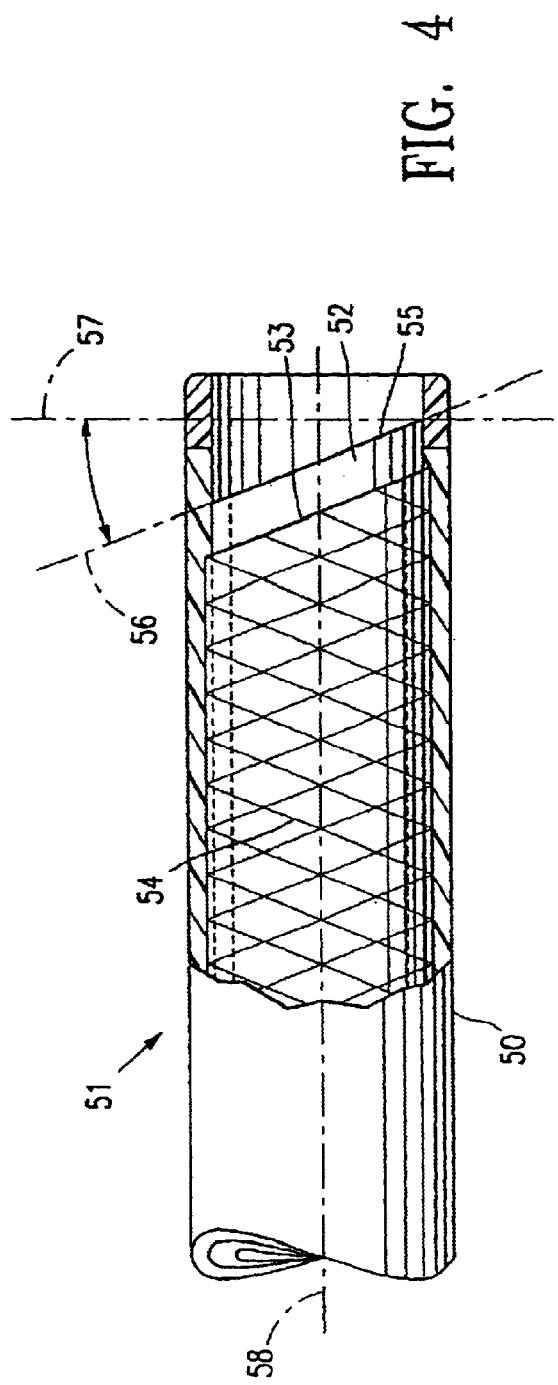

GUIDING CATHETER REINFORCEMENT WITH ANGLED DISTAL END

BACKGROUND OF THE INVENTION

This invention generally relates to the guiding catheters for advancing and delivering intraluminal therapeutic and diagnostic devices within a patient's body lumen and more specifically to a guiding catheter for providing coronary artery access for a variety of coronary procedures including angioplasty, stent delivery and the like.

In a typical coronary procedure, a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. An elongated therapeutic or diagnostic device such as a balloon dilatation catheter or a stent delivery catheter are advanced through the inner lumen of the guiding catheter into one of the patient's coronary arteries.

Further details of devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson et al.) which are hereby incorporated herein in their entirety by reference thereto.

The typical guiding catheter has an inner tubular layer and outer tubular layer and a tubular reinforcing layer of braided wire or ribbon disposed within the wall defined by the inner and outer layer. Frequently, the braided reinforcement layer is embedded in one or both of the inner and outer layers depending upon the manufacturing processing utilized. The distal tip of the guiding catheter is preferably formed of relatively soft polymeric material to avoid traumatic engagement with the walls or the blood vessel or the coronary ostium. The soft tip may be formed of a separate tip which is secured to the distal end of the catheter or may be an extension of one or more of the layers that form the catheter walls. Typically, the braided reinforcement layer terminates proximal to the distal end of the guiding catheter and the distal end of the reinforcement layer lies in a plane perpendicular to the longitudinal axis of the catheter. The ends of the individual wires or strands at the distal end of the braided reinforcement are welded or otherwise secured to adjacent braided structure.

During the course of an intraluminal procedure, an intraluminal device, such as a balloon catheter, atherectomy catheter, and the like, may be introduced through the guiding catheter into the vessel or body lumen. Following the intraluminal procedure, the intraluminal device is usually withdrawn through the guiding catheter distal tip. Frequently, however, the operating portion of the intraluminal device presents a larger profile upon withdrawal than when delivered. For example, with balloon catheters for angioplasty or stent delivery, the balloons on the catheters are larger in one or more transverse dimensions after inflation than when passing through the guiding catheter which can make the withdrawal of the deflated balloon back into the interior of guiding catheter problematic. Withdrawal of the intraluminal device into the guiding catheter and then withdrawal of the guiding catheter and the device together is usually preferred.

What has been needed is some way to facilitate reentry of the intraluminal device back into the inner lumen of the guiding catheter. The present invention satisfies these and other needs.

SUMMARY OF THE INVENTION

The invention is generally directed to a guiding catheter for delivery of intraluminal devices which has an elongate tubular body with a multistrand braided reinforcing structure disposed within the wall forming the tubular body. The distal end of the braided reinforcing structure lies in a plane at an angle with respect to the longitudinal axis of the tubular body of the catheter that deviates from a plane perpendicular to the longitudinal axis. The deviation angle for the distal end should be at least 10° preferably at least 30° from the plane perpendicular to the catheter axis. This braided reinforcing structure facilitates the retraction of an intraluminal device, such as a balloon catheter for angioplasty or stent delivery. The angle of the braid opening may follow the braid lay-up angle (the angle characteristic of the wire or ribbon comprising the braided reinforcing layer), or may be at an angle independent of the lay-up angle. The strands (wires or ribbons) of the braided reinforcement may be bonded or welded at the braid terminal end to bond the individual wires or ribbons to the adjacent wires or ribbons.

The guiding catheter of the invention comprises a tubular reinforcing layer of braided wire or ribbon disposed about an inner layer and an outer layer disposed about the braided reinforcement layer. The distal end of the guiding catheter, i.e. the portion distal to the braided reinforcement layer is formed of relatively soft material to prevent traumatic engagement with the lining of body lumens through which the guiding catheter is advanced. The reinforcement layer has a plurality of wires or ribbons braided about the inner layer at a characteristic braid angle, typically in a plurality of interwoven helices of both clockwise and counterclockwise orientation with respect to the longitudinal axis of the catheter. Conventional braiding mechanisms may be used to produce the braided layer.

The distal end of the braided reinforcement is at an angle with respect to the longitudinal axis of the catheter so the opening at the distal end of the braided reinforcement presents a generally elliptical opening with a greater surface area than an opening which lies in a plane perpendicular to the longitudinal axis which is generally circular in shape. Note that the "opening" referenced is the effective end of the braided reinforcement, since typically the softer and more compliant tip material and/or liner extends distally of the braid. The angled and larger opening in the braided reinforcement provides less abrupt and easier transition for the balloon or other device being withdrawn into the catheter, and thus assists the withdrawal. The inner liner may also have an similarly angled terminal end. The portion of the catheter distal to the angled distal tip of the braided reinforcement structure is pliable enough so that it does not interfere significantly with the expanded distal opening provided by the angled distal tip of the reinforcement.

These and other advantages of the invention will become more apparent from the following detailed description of the invention and the accompanying exemplary drawings.

BRIEF DESCRIPTION OF THE DRAWINGS

FIG. 3 is a longitudinal elevational view, similar to that of FIG. 2 of the distal shaft section of a guiding catheter which embodies features of the invention.

FIG. 4 depicts a longitudinal elevation view of an alternative guiding catheter having features of the invention with the outer layer removed to illustrate the braided reinforcement and inner tubular layer.

DETAILED DESCRIPTION OF THE INVENTION

Figure 1:
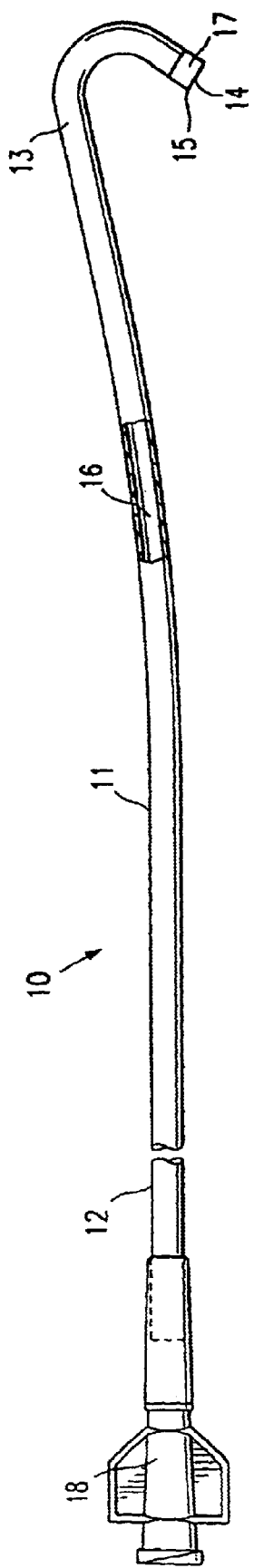
FIG. 1 is a schematic elevational view, partially in section of a conventional guiding catheter.

FIG. 1 schematically depicts an elevational view of a conventional guiding catheter 10 having an elongated shaft 11 with a proximal section 12, a distal section 13, a port 14 in the distal end 15 and an inner lumen 16 extending therein to an in fluid communication with the port 14 in the distal end. The distal section 13 is usually provided with a particular shape which facilitates advancement to and seating within the desired opening within the patient's body such as a coronary ostium. A soft tip 17 is provided on the distal end 15. An adapter 18 is provided on the proximal end of the catheter to provide access to the inner lumen 16. A variety of adapters may be utilized including adapters having one or more side arms for providing flushing fluids, radiopaque fluids and the like.

Figure 2:
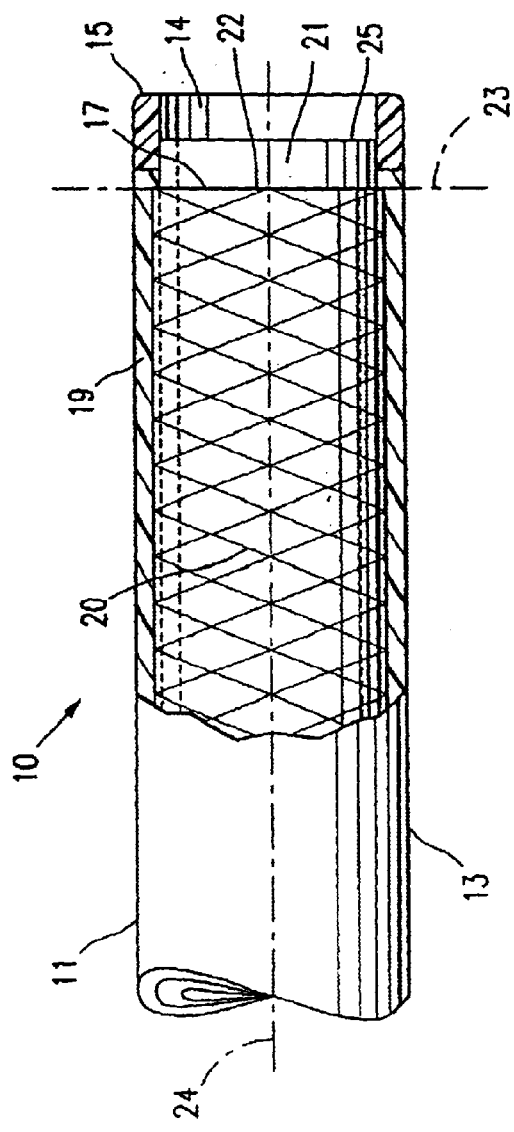
FIG. 2 is a longitudinal elevation view of the distal shaft section of a prior art guiding catheter with the outer layer partially removed to expose the braided reinforcement layer.

FIG. 2 is an enlarged longitudinal elevation view of the distal section of the prior art guiding catheter 10, with the outer layer 19 being partially removed to expose the braided reinforcement layer 20 surrounding the inner layer 21. To simplify the drawings it should be noted that the distal section 13 is shown as being straight in FIG. 2 whereas it is shown as being curved in FIG. 1. Moreover, the individual strands of the reinforcement layer are shown as lines, whereas they maybe formed wires or ribbons of high strength materials. The braided reinforcement layer 20 terminates proximal the distal tip 15 of the catheter shaft 11 and the distal end 22 of the braided reinforcement layer 20 lies in a plane 23 which is generally perpendicular to the longitudinal catheter axis 24. The inner layer 21 extends beyond the distal end of the reinforcement layer 20 and has a distal end 25.

FIG. 3 depicts a distal section 30 of a guiding catheter 31 embodying features of the invention which generally has an elongated shaft 32 such as that shown in FIG. 1, an inner layer FIG. 3 depicts a distal section 30 of a guiding catheter 31 embodying features of the invention which generally has an elongated shaft 32 such as that shown in FIG. 1, an inner layer 33, a multistrand braided reinforcement layer 34 disposed about the inner layer and an outer layer 35 disposed about the braided reinforcement layer 34. The multi-strand braided reinforcement layer 34 has a distal end 36 which lies in a plane 37 at an angle with respect to a transverse plane 38 (shown in phantom) perpendicular to the longitudinal axis 39. The multiple layered wall structure of the elongated shaft 32 shown generally has the same structure as that shown for the catheter of FIGS. 1 and 2 including having an adapter on the proximal end of the shaft and a curved distal shaft section 30. The braided reinforcement layer 34 terminates adjacent the distal soft tip 40. In the embodiment shown in FIG. 3, the liner layer 33 term mates adjacent the port 41 in a distal end 42 which lies in a transverse plane generally perpendicular to the catheter axis. The opening defined by the angled distal end 36 of the braided reinforcement layer is projected outwardly in a plane parallel to the angled plane 37 which has been rotated 90° to show the elliptical shape 43 presented by the opening in the distal end 36. This provides a substantial increase in the opening area which facilitates entry of the operating ends of intraluminal devices back into the inner lumen 43 of the guiding catheter 31.

Table 1 below compares the increase in effective entrance area of the braid layer distal end opening based on the angle on the opening relative to the catheter axis. The example of Table 1 is a No. 8 French guiding catheter with an inside diameter of 0.088 in. (2.2 mm). Table 1 shows that for an angle of 15°, the area is increased by about 3%. For larger angles the increase in area is greater. As the angle exceeds 30 degrees, the increase in effective entrance area exceeds 10%.

Note that this is the increase in the opening area of the braided reinforcement layer itself. Because the braid lies outside the liner, cross-section of the lumen is smaller than the area of the braid opening even at 0%. Thus, for substantially non-perpendicular angles (of about 15° or greater from the perpendicular), the opening angle of the tip provides an effective tip opening area substantially larger than the cross section of the lumen itself. The angle may be selected to produce the desired increase in area and the desired improvement in the pull-back or retraction function.

TABLE 1

| Area Increase vs. Angle | | |
|---|---|---|
| Angle | Area (in$^2$) | % Increase |
| 0 | 0.0061 (3.94 mm$^2$) | 0 |
| 15 | 0.0063 (4.06 mm$^2$) | 3 |
| 30 | 0.0067 (432 mm$^2$) | 10 |
| 45 | 0.0086 (5.55 mm$^2$) | 41 |

Thus, it is clear that the guide catheter of the invention provides for increased braid end opening area to assist in the withdrawal of an intraluminal device. By the same principal, the end opening of the liner layer may also be increased.

The embodiment shown in FIG. 4 illustrates an alternative construction to the distal shaft section 50 of a guiding catheter 51 embodying features of the invention. In this alternative construction the inner layer 52 extends beyond the angled distal end 53 of the braided reinforcement layer 54 and has a distal end 55 which lies in a plane 56 which is at an angle with respect to a transverse plane 57 perpendicular to the longitudinal axis 58. The angled distal end 55 to the inner layer 52 may be aligned with the angled distal end 53 of the braided reinforcement layer 54 or at another substantial angle to the transverse plane 57 which is perpendicular to longitudinal axis 58.

Guiding catheters designed for coronary artery access generally have a length from about 90 to about 110 cm, preferably about 100 cm. The wall thickness of the catheter shaft ranges from about 0.004 to about 0.01 inch. (0.1–0.25 mm) The outer polymeric layer is about 0.001 to about 0.006 inch (0.025–0.15 mm) and the inner polymeric layer is about 0.001 to about 0.002 inch (0.025–0.005 mm). The presently preferred polymeric materials are various durometers of PEBAX or nylon. Other suitable polymeric materials include polyimide and polyurethanes. A variety of other thermoplastic and thermoelastic polymers, copolymers and blends may be employed.

The strands which are braided to form the braided reinforcement layer may have a round (wire) or rectangular (ribbon) and their transverse dimensions depends upon the mechanical properties and the stiffness required for the braided reinforcement layer. For stainless steel wire a diameter of about 0.001 to about 0.003 inch (0.025–0.076 mm) is suitable. For stainless steel ribbon, the transverse cross sectional dimensions are about 0.0005 to 0.002 inch (0.013–0.051 mm) by about 0.003 to about 0.01 inch (0.076–0.054 mm). The maximum wall thickness of the braided reinforcing structure will be located at the cross points of the strands. The transverse and longitudinal dimensions of the catheter, the materials of construction, the number and spacing of the reinforcing strands will vary depending upon the end use of the catheter. The strands forming the braided reinforcement layer can be formed of a variety of materials include stainless steel (304) and high strength alloys such as MP35N, Elgiloy and L-605 which contain cobalt, chromium and nickel. The high strength alloys generally contain about 28 to about 65% cobalt, about 2 to about 40% nickel, about 5 to about 35% chromium and preferably also contain up to about 12% molybdenum, up to about 20% tungsten, up to about 20% iron and inconsequential amounts of other elements either as positive additions or impurities. The high strength alloy strands are preferably precipitation hardened for optimum properties. High strength plastic strands (e.g. Kevlar) or mixtures of plastic and metallic strands may also be used to form the braided reinforcing structure. Other metallic materials include superelastic NiTi alloys.

The adapter on the proximal end of the catheter and the nose piece for the adapter may be formed of conventional polymeric materials such as polycarbonate.

The inner layer of the catheter shaft is preferably formed of lubricous material or have a lubricious inner surface. The presently preferred lubricious material is a fluoropolymer. The outer layer is preferably a polyamide elastomer, e.g. a polyether block amide such as PEBAX 55 alone or blended with nylon or PEBAX materials with other durometers.

The materials of construction and catheter design not otherwise referred to herein can follow conventional technology. Moreover, while particular forms of the invention have been illustrated and described, it will be apparent that various modifications can be made to the invention. It will also be apparent from the foregoing that those skilled in the art will recognize that features shown in one embodiment may be utilized in other embodiments.

What is claimed is:

1. A guiding catheter for intracorporeal deployment of an elongated medical device within a patient's body lumen, comprising:
   a) an elongate tubular catheter shaft having a proximal section, a distal section, an inner lumen extending therein to a port in a distal end, and a longitudinal axis;
   b) an inner layer defining at least in part the inner lumen; and
   c) an elongated multi-strand braided reinforcing layer disposed about the inner layer and having a terminal distal end cut which lies in a transverse plane at an angle with respect to a transverse plane perpendicular to the longitudinal axis.

2. The guiding catheter of claim 1 including an outer layer disposed about the multistrand braided reinforcing layer.

3. The guiding catheter of claim 1, wherein the distal end of the multi-strand braided reinforcing layer lies in a plane at an angle of at least about 15° from the transverse plane perpendicular to the longitudinal axis.

4. The guiding catheter of claim 1, wherein the inner layer has a terminal distal end which lies in a transverse plane aligned at an angle with respect to a transverse plane perpendicular to the longitudinal axis.

5. The guiding catheter of claim 4, wherein the terminal distal end of the inner layer lies in a transverse plane aligned at an angle at least about 15° from the transverse plane perpendicular to the longitudinal axis.

6. The guiding catheter of claim 3 including a distal tip formed of soft polymeric material distal to the distal end of the braided reinforcing layer and the distal end of the inner layer opening.

7. The guiding catheter of claim 3, wherein the strands of the multi-strand braided reinforcement layer are selected from the group of wires and ribbons.

8. The guiding wire of claim 1, wherein the strands of the multi-strand braided reinforcement layer are at a preselected braid angle.

9. The guiding catheter of claim 3, wherein the distal end of the multi-strand braided reinforcement layer is at an angle substantially the same as the braid angle.

10. The guiding catheter of claim 3, wherein the distal end of the multi-strand braided reinforcement layer is at an angle substantially distinct from the characteristic braid angle.

11. The guiding catheter of claim 10, wherein the distal end of the multi-strand braided reinforcement layer is at an angle of at least 5° from the preselected braid angle.

12. A catheter comprising:
   a hollow catheter shaft having a proximal section, a distal section and an inner layer wherein the shaft defines a longitudinal axis; and
   a braid disposed about the inner layer, the braid having a terminal distal end cut at an angle with respect to a transverse plane perpendicular to the longitudinal axis of the catheter shaft.

13. The catheter of claim 12 further comprising an outer layer disposed about the braid.

14. The catheter of claim 12, wherein the cut angle of the distal end of the braid is at least about 15 degrees from the transverse plane perpendicular to the longitudinal axis.

15. The catheter of claim 12, wherein the inner layer has a distal end disposed in a transverse plane aligned at an angle with respect to the transverse plane perpendicular to the longitudinal axis of the shaft.

16. The catheter of claim 15, wherein the distal end of the inner layer lies in a transverse plane at least about 15 degrees from the transverse plane perpendicular to the longitudinal axis of the shaft.

17. The catheter of claim 12, wherein the braid includes strands disposed at a braid angle.

18. The catheter of claim 17, wherein the cut angle of the distal end of the braid is substantially the same as the braid angle.

19. The catheter of claim 17, wherein the cut angle of the distal end of the braid is substantially different from the braid angle.

20. The catheter of claim 19, wherein the cut angle of the distal end of the braid is at least five degrees different from the braid angle.

* * * * *

UNITED STATES PATENT AND TRADEMARK OFFICE
CERTIFICATE OF CORRECTION

PATENT NO. : 6,740,073 B1
DATED : May 25, 2004
INVENTOR(S) : Steven T. Saville

It is certified that error appears in the above-identified patent and that said Letters Patent is hereby corrected as shown below:

Column 2,
Line 10, change "should be at least 10º"" to -- should be at least 10º, --
Lines 48 and 49, change "may also have an similarly" to -- may also have a similarly --

Column 3,
Lines 38-41, delete "FIG. 3 depicts a distal section 30 of a guiding catheter 31 embodying features of the invention which generally has an elongated shaft 32 such as that shown in FIG. 1, an inner layer"

Column 4,
Line 28, change "0.0067 (432 mm$^2$)" to -- 0.0067 (4.32 mm$^2$) --

Signed and Sealed this

Fourth Day of January, 2005

JON W. DUDAS
*Director of the United States Patent and Trademark Office*